(12) United States Patent
Afilani

(10) Patent No.: US 6,674,366 B1
(45) Date of Patent: *Jan. 6, 2004

(54) INANIMATE ENTITY LINE-OF-BEARING LOCATION METHOD VIA LINKING MATERIAL-SPECIFIC NON-UNIFORM STATIC ELECTRIFICATION SPATIAL GRADIENT PATTERN TO DIELECTROPHORESIS

(75) Inventor: Thomas L Afilani, Jersey Shore, PA (US)

(73) Assignee: DKL International, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/071,825

(22) Filed: May 4, 1998

Related U.S. Application Data

(63) Continuation-in-part of application No. 08/758,248, filed on Nov. 27, 1996, now Pat. No. 5,748,088.

(51) Int. Cl.$^7$ .............................................. G08B 23/00
(52) U.S. Cl. .................... 340/573.1; 340/561; 340/562; 340/568.1; 324/71.1; 324/72; 324/452; 324/457
(58) Field of Search .............................. 340/573.1, 561, 340/562, 563, 564, 565, 566, 567, 568.1; 324/71.1, 72, 452, 457

(56) References Cited

U.S. PATENT DOCUMENTS

| | | |
|---|---|---|
| 3,771,152 A | 11/1973 | Dettling et al. |
| 3,836,899 A | 9/1974 | Duvall et al. |
| 3,898,472 A | 8/1975 | Long |
| 4,138,641 A | 2/1979 | Karlin et al. |
| 4,316,180 A | 2/1982 | LeVert |
| 4,320,766 A | 3/1982 | Alihanka et al. |
| 4,339,709 A | 7/1982 | Brihier |
| 4,476,004 A | * 10/1984 | Pohl ........................ 435/285.2 |

(List continued on next page.)

FOREIGN PATENT DOCUMENTS

| | | |
|---|---|---|
| JP | 1-113692 | 5/1989 |
| WO | WO 98/24077 | 6/1998 |

OTHER PUBLICATIONS

Keiichi, M. "Detecting Circuit Of Signal," Patent abstacts of Japan, vol. 007, No. 278, (p. 242), Dec. 1983 & JP 58 154671 A (Sep. 1983).
Murray, Dale W., "Physical Examination of the DKL Life-Guard™ Model 3," Oct. 30, 1998, (pp. 1–53).

(List continued on next page.)

*Primary Examiner*—Nina Tong
(74) *Attorney, Agent, or Firm*—Nixon & Vanderhye P.C.

(57) ABSTRACT

The dielectrophoretic force caused by the non-uniform electric field squared spatial gradient three-dimensional pattern uniquely exhibited by a predetermined type of inanimate entity can be detected by a locator device. A human operator holds the device in hand to thereby electrically and dielectrically connect the device to the human operator. The human operator's naturally occurring very low electrical decay time constant is increased through electronic circuitry externally connected to the device. The device is held in a balanced nearly horizontal state, and the operator scans the device in a constant speed uniform linear motion back and forth. An antenna extends from the front of the device, and both are acted on by the dielectrophoretic force. This force results in a subsequent resulting torque, acceleration, vibration or any other measurable quantifiable manifestation of the force about the handle's pivot line hence driving the device and its antenna toward the direction and position of any inanimate entities of the predetermined type that are within range.

16 Claims, 12 Drawing Sheets

U.S. PATENT DOCUMENTS

| | | | | |
|---|---|---|---|---|
| 4,621,258 A | | 11/1986 | Campman | |
| 4,632,762 A | | 12/1986 | Ramsland | |
| 4,956,065 A | * | 9/1990 | Kaler et al. | 204/547 |
| 5,019,804 A | | 5/1991 | Fraden | |
| 5,300,889 A | * | 4/1994 | Bakhoum | 324/457 |
| 5,436,613 A | | 7/1995 | Ghosh et al. | |
| 5,446,591 A | | 8/1995 | Medlock | |
| 5,748,088 A | * | 5/1998 | Afilani | 340/573.1 |
| 6,264,815 B1 | * | 7/2001 | Pethig et al. | 204/547 |

OTHER PUBLICATIONS

Murray, Dale W. et al., "Double–Blind Evaluation of the DKL LifeGuard Model 2," Apr. 29, 1998, (21 pages).

Moore, A. D., "Electrostatics and its Applications," Electrical and Computer Engineering Dept., University of Michigan, Ann Arbor, (4 pages).

Pohl, Herbert A., "Dielectrophoresis: The Behavior of Neutral Matter in Nonuniform Electric Fields," (7 pages).

The New Lexicon "Webster's Encyclopedic Dictionary" of the English Language, (definitions of "electrokinetics," "electrophoresis," "kinesis," and "kinetics" ; (5 pages).

Voss, D., "New Physics' Finds a Haven at the Patent Office," Science, vol. 284, May 21, 1999 (pp. 1252–1254).

\* cited by examiner

Correlation between electric resistivity and dielectric control of polymers

INANIMATE ENTITY LINE-OF-BEARING LOCATION METHOD VIA LINKING MATERIAL-SPECIFIC NON-UNIFORM STATIC ELECTRIFICATION SPATIAL GRADIENT PATTERN TO DIELECTROPHORESIS

This application is a continuation-in-part of U.S. patent application Ser. No. 08/758,248, filed Nov. 27, 1996, now U.S. Pat. No. 5,748,088.

BACKGROUND OF THE INVENTION

This invention relates to the fields of dielectrophoresis phenomena, inanimate material non-uniform surface electric field patterns and spatial gradient patterns caused by naturally-occurring static electrification. More particularly, the invention relates to the hitherto unattainable detection and location of inanimate materials by coupling the non-uniform electric field spatial gradient pattern via dielectrophoresis to a characteristic force and subsequent torque on a high aspect ratio (length/radius) antenna and selective dielectric polarization matching and filtering components in a locating device giving a real-time updated line-of-bearing to the inanimate material maximum surface electric field spatial gradient and hence to the inanimate entity itself, even if an entity is located behind vision-obscuring barriers made of metals, dielectrics, plastics, earth, wood, etc. and/or EMI is present.

The detection of visually obscured entities has many uses in fire-fighting, search and rescue operations, law enforcement operations, military operations, etc. With respect to inanimate entities, such as specific polymers, plastics, and other organic/inorganic materials, additional applications may include transportation security in pre-boarding planes, trains and automobiles, new and old construction industry, law enforcement, military operations, anti-shoplifting protection and other security needs/operations. While prior art devices are known that detect humans, animals and other materials, some by measuring changes in an electrostatic field, none of the operable prior art devices uses the force resulting from the non-uniform electric field squared spatial gradient three-dimensional pattern exhibited uniquely by an entity to indicate the precise location and direction of the subject entity relative to the device's operator.

By using an electrokinetic effect, dielectrophoresis, which induces a force and subsequent resulting torque on an antenna and other component parts of the device, the present invention gives a rapid directional location indication of the subject entity. A meter can also be provided to indicate the direction of strongest non-uniform electric field squared spatial gradient signal strength for those situations where the dielectrophoretic force and subsequent resulting torque, acceleration, vibration or any other measurable quantifiable manifestation of the force is extremely small and difficult to detect.

It should be noted that while the present invention works for many different types of entities, a primary use of the present invention is to locate inanimate entities, irrespective of the presence or absence of obscuring material structures (walls, trees, earthen mounds, etc.), rfi and emi interference signals, adverse weather conditions, and day or night visibility conditions.

Dielectrophoresis describes the force and subsequent torque mechanical behavior of initially neutral mater that is dielectric polarization charged via induction by external spatially non-uniform electric fields. The severity of the spatial non-uniformity of the electric field is measured by the spatial gradient (spatial rate of change) of the electric field. The fundamental operating principle of the dielectrophoresis effect is that the force (or torque) generated always seeks to point in the same direction, toward the maximum local electric field spatial gradient, independent of sign (+/−) or time (AC/DC). See, H. A. Pohl, *Dielectrophoresis*, Cambridge University Press (1978) and H. A. Pohl, *Electrostatics and Applications*, Chapters 14 and 15, A. D. Moore (editor), Interscience Press (1973).

The nature and source of the inanimate entity's (in particular plastics) electric field and its spatial gradient being detected in the dielecrophoresis effect generating the directionally self-correcting force and subsequent torque characteristic of an animate entity line-of-bearing locating device has been discussed in *Static Electrification*, P. Secker, University College North Wales (1976); D. J. Montgomery, *Static Electrification of Solids*, Solid State Physics, 9, 139 (1959); W. R. Harper, *Contact and Frictional Electrification*, Oxford Press (*1967*); R. Cunningham, *Static Electrification*, Physics Encyclopedia, 891 (1974); I. Inculet in *Electrostatics and Applications*, Chapter 5, supra; G. H. Johnson, *Polymer Films Static Electrification*, DuPont (1974 to 1979). The empirical evidence in the case of inanimate materials is quite persuasive that the inanimate objects' naturally-occurring static electrification generates a small ULF ($10^{-3}$ Hz to 2 Hz) electric field and spatial gradient pattern.

Static electrification proceeds via naturally-occurring contact charging (static/dynamic) including transfer of electrons, ions, charged chemical species and via the intimate interfacial phenomena triboelectric charging. Static electrification also proceeds via artificially-occurring industrial processes using static charging by corona, flame, electron beam, radiation and induction. Static electrification phenomena occur in industrial and domestic life via highly insulating nonconducting materials such as polymers and plastics.

Naturally-occurring static electrification via wind and water currents causes detection information transfer allowing orientational/navigational abilities and activities of birds, bees and fish. See, *Electromagnetic Bio-Information*, F. Popp, et al. (eds.), Urgan Publ. (1979); *Handbook: Biological Effects of Electromagnetic Fields*, C. Pol, CRC Press (1966) *Sensory Biology of Aquatic Animals*, J. Aetma, et al. (eds.), Springer (1988); *Orientation: Sensory Basis*, H. E. Adler, 188, 271 91971). For semi-conducting human bodies, but not for highly insulating plastics, static electrification effects, while nuisances, are short-lasting effects, neutralized by RH, or leaked to the ground. Bulk human decay times are about $10^{-3}$ sec.

The very high electrical resistivity of widely-used plastics as materials-of-construction does not allow the static electrification charges to leak harmlessly to ground. On the contrary, the charges are continuously accumulated at a particular location or on the surface building up very high electrical surface voltages up to tens of kilovolts. The static electrification charges on plastics are very long-lasting, with characteristic times for exponential decay of $10^2$ sec. (polyester) to $10^6$ sec (Teflon®) (minutes to days). This is generally referred to as sub-ULF (0 to 3 Hz) and ULF (3 to 30 Hz) frequencies. In the ULF and sub-ULF ranges as discussed in D. O. Carpenter, *Biolozical Effects of Electromagnetic Fields*, Academic Press (1994), the electric and magnetic fields are quasi-static, are not strongly coupled as "EM waves," and EM activity detected in this range have predominantly either electric or magnetic nature. See J.

Heirtzler, *Sci. Am.* 205, 3, 128 (1962); S. Mende, *Sci. Am.* 204, 8 (1997); S. Carlson, *Sci. Am.* 239, 5, 98 (1996). The voltage decay time constant depends on the material's inherent electrical resistivity and dielectric constant describing plastics conduction and polarization properties as discussed in *Properties of Polymers*, D. van Krevelen, Elsevier Publ. (1976); A. R. von Hippel, *Dielectrics and Waves*, John Wiley and Sons (1954); and *Dielectric Materials & Applications*, A. R. von Hippel, John Wiley (1954). The irregular, pervasive nature of static electrification ensures long-lasting electric field patterns having significant spatial gradients. The voltages, electric fields and electric field spatial gradient decrease as one moves away from the surface of the plastics material. In addition, various surface free/bound-charge electron traps exist on all materials, particularly plastics. See, *Physical Chemistry of Surfaces*, A. W. Adamson, Interscience Publ. (1967); *Excess Electrons in Dielectric Media*, C. Ferradini (ed), CRC Press (1991).

Static electrification effects are further divided into threshold and non-threshold type phenomena. Dust and debris accumulation, as well as "static cling" are examples of non-threshold static electrification effects as are the build-up of surface voltage, electric field and electric field spatial gradient. Other static electrifcation effects, like electrical discharges, spurious images, capacitor breakdown, explosions and anomalously strong adhesion, are examples of threshold effects. Static electrification voltage effects (electric fields and electric field gradients on dielectric materials, particularly plastics, charge-up following an exponential build-up equation:

$$V(t)=V_0(1-e^{-t/\tau}) \text{ and discharge as } V(t)=V-e^{-t/\tau}$$

wherein $\tau$=time constant with three components: $1/\tau=1/\tau_B + 1/\tau_S + 1/\tau_R$ where $\tau_B$=bulk time constant, $\tau_S$=surface time constant, and $\tau_R$=irradiation time constant. The bulk time constant is related to the bulk electrical resitivity ($\rho$) and K, the bulk dielectric constant, via: $\tau_B = \rho K \in_0$; $\in_0$=free space permittivity =$8.85 \times 10^{-12}$ farad/m. The surface time constant is related particularly to the inverse of the relative humidity in the atmosphere. The radiation time constant is related particularly to the inverse of the amounts of positive and negative charged species in the atmosphere. For example, Polonium 210 is a prolific source of both positively and negatively charged nuclear species, providing for a very short irradiation time constant.

The dependent variable of interest for the present invention is the levels and time dependence of the surface voltage, electric field and electric field spatial gradient. These dependent variables are considered as functions of numerous independent variables: material variables (bulk and surface chemical composition and structure; bulk and surface electrical resistivities, contact potential differences and dielectric constants; molecular and structure, orientation and crystallinity; state of strain; size and shape; initial state of electrical charge); ambient conditions (relative humidity, temperature, atmospheric composition and pressure and presence of stray, interfering electromagnetic fields (EMI)); and mechanical variables (type of contact (touching, impacting, rubbing, rolling, twisting, etc.); orientation of bodies during contact; area of contact (including path length); duration of contact; relative velocity of materials; normal and tangential forces between the materials). The static electrification build-up and time dependence and decay of the surface voltage, electric field and spatial gradient are due to excess charge transfer and its future behavior.

Traditionally, inanimate dielectrics have been found to exhibit three main and one rare polarization modes (electronic, atomic, orientation and the rare nomadic) as discussed in *Properties of Polymers*, D. W. van Krevelen, Elsevier Publ. (1976); A. R. von Hippel, *Dielectrics and Waves*, John Wiley and Sons (195); *Dielectric Materials & Applications*, A. R. von Hippel (ed) John Wiley (1954); H. A. Pohl, *Dielectrophoresis*, Cambridge University Press (1978). These modes lead additively in the sequence given as one goes from UHF ($10^{18}$ Hz) to ULF (3 to 30 Hz) to sub-ULF (0 to 3 Hz) dielectric constraints of 1.0 for air to 78 for water with essentially all plastics in a 3 (PVC) to 14 (Bakelite) range. There are rare outriders like the solvent NMMA at 191, Se at $1 \times 10^3$ and ferroelectric $BaTiO_3$ and rare nomadic polymers $(CS_2)_x$ at $2 \times 10^4$ and PAQR carbazole at $3 \times 10^5$.

Mammalian physiology results for the ULF dielectric constants of mammalian (human) living tissues, wherein mammalian (human) tissues are 70% volume water (dielectric constant 78), show that all the ordinary animate human tissues, like heart, brain, liver, heart, blood, skin, lung and even bone, have quite extraordinarily very high ULF dielectric constants ($10^5$ to $10^7$), found only very rarely in usual inanimate dielectric materials. See *Biomedical Engineering Handbook*, J. D. Bronzino (ed.), CRC Press (1995); *Physical Properties of Tissue*, F. A. Duck, Academic Press (1990); H. P. Schwan, *Advances in Biological and Medical Physics*, 5, 148 to 206 (1957); E. Grant, *Dielectric Behaviour of Biological Molecules*, Oxford Univ. (1978). It is also found that, as the animate tissues die, these extraordinarily high ULF dielectric constant collapse downward greatly to more normal inanimate values over time as the dying tissue becomes over time inanimate. The reason for the great differences is the routine occurrence of other polarization modes in animate materials, but which occur very rarely in inanimate materials. These other polarization modes are interfacial (inhomogeneous materials) and pre-polarized elements which occur readily in all animate tissues. It is known that the rest state of the human neural, cardiac, skeletal muscular and sensory systems are states of high polarization. Therefore, the extraordinarily high dielectric constant for the human operator causes the static electrification electric field lines and spatial gradients to be directionally distorted toward a human operator of the locator device, hence increasing the electric field line flux density, which is directly related to an increase in the device's sensitivity.

Dielectrophoresis has been practiced using nearly exclusively artificially-set-up external non-uniform electric field patterns in laboratories to dielectrically separate individual em-size mammalian cells or small ($\mu$m) inanimate, inorganic particles. See, H. A. Pohl, *Dielectrophoresis*, Cambridge University Press (1978) and T. B. Jones, *Electromechanics of Particles*, Cambridge University Press (1995). The problems of this prior art in trying to observe dielectrophoresis force and torque effects in meter-size ensembles of tens of billions of $\mu$m-size inorganic particles chemically coupled together and working in concert as an inanimate entity are overcome by utilizing naturally-occurring pervasive static electrification effects—surface ULF electric fields and electric field spatial gradients. Table I lists the charging and discharging time constants for some well known plastic materials.

FIG. 1 illustrates static electrification of an inanimate entity 10; where material one 11 and material two 12 are in mutual and intimate contact with inanimate entity 10 at interfaces 13 and 14, respectively, moving at speed $V_1$ and $V_2$ with respect to the inanimate entity 10. The amount and sign of the electrical charges (voltages, electric fields and electric field spatial gradient) exchanged at the two interfaces 13, 14 via static electrification depends upon the relative positions of the materials 11, 12 and the inanimate entity 10 on the triboelectric series 20 (and other factors), wherein positions on the triboelectric series are determined by the dielectric constant 21 and environmental conditions (dry or wet). See FIG. 2. The static electrification charging and discharging time constants $\tau$ of materials 11, 12 and inanimate entity 10 depend also upon their bulk electrical resisitivites $\rho$ via equation $\tau = \rho K \in_0$ as previously discussed.

FIG. 3 shows the correlation between bulk electrical resistivity $\rho$ 31 and the dielectric constant K 32. The bulk charging and discharging time constant ($\tau$) is related to these factors via the equation $\tau = \rho K \in_0$; where $\in_0$=free space permittivity=$8.85 \times 10^{12}$ F/m and unit for $\rho$ is $(\Omega\text{-m})^{-1}$. Note F/$\Omega$=sec. FIG. 4 shows a typical static electrification electric field spatial gradient where a positively charged 40 polymer web 41 has a very uniform electric field lines 42, (low electric field spatial gradient), far from the a grounded metal roller 43, but near the grounded metal roller 43, the electric field lines 44 become very low over a very short spatial distance, creating an extremely large spatial gradient for the electric field lines just as the positively charged 40 polymer web 41 enters the "nip" 46 of the grounded metal roller 43.

FIGS. 5(a) and 5(b) show the exponential growth 51 and decay 52 curves, respectively for surface voltage, electric field (spatial gradients) resulting from the static electrification and de-electrification of an (see FIG. 1) inanimate entity's 10 surface by the materials 11 and 12, with which it is in mutual and intimate contact. FIG. 6 shows ideal ULF waveform 60 for repeated charge 61 and discharge 62 cycles due to static electrification and de-electrification of the surface of an inanimate entity 10 by the materials 11 and 12.

SUMMARY OF THE INVENTION

The present invention relates to a locator device that detects the presence of various entities using an electrokinetic effect known as dielectrophoresis. Dielectrophoresis is one of five known electrokinetic effects (the other four being electrophoresis, electro-osmosis, Dorn effect, and streaming potential) and describes the forces affecting the mechanical behavior of initially neutral matter that is dielectrically polarized by induction via spatially non-uniform electric fields. The spatial non-uniformity of an electric field can be measured by the spatial gradient of the electric field. The dielectrophoresis force depends non-linearly upon several factors, including the dielectric polarizibility of the surrounding medium (air plus any intervening walls, trees, etc.), the dielectric polarizibility and geometry of the initially neutral matter (device's antenna and other component parts of the device), and the spatial gradient of the square of the target's local electric field distribution induced by static electrification as detected at the device's antenna and other component parts. The spatial gradient is measured by the dielectrophoresis force produced by the induced polarization charge on the device's antenna and other component parts, and this force is a constant direction seeking force always pointing (or trying to point) the device's antenna and other component parts toward the maximum gradient in the three-dimensional non-uniform electric field squared spatial gradient pattern uniquely exhibited by a predetermined entity type.

The constant direction seeking force is highly variable in magnitude as a function of the angular position and radial position of the entity-to-be-located with respect to the device's antenna and other component parts of the device, and upon the effective dielectric polarizibilities of the intervening medium (like air) and of the materials used in the device's antenna and other component parts. The following equations define the dielectrophoresis forces wherein Equation 1 shows the force for spherical initially neutral objects (spherical antenna and the device's other component parts), and Equation 2 shows the force for cylindrical initially neutral objects (cylindrical antenna and the device's other component parts).

$$F = 2(\pi a^3) \in_0 K_1 (K_2 - K_1)/(K_2 + 2K_1) \nabla |E_0|^2 \qquad \text{Equation 1}$$

$$F = L/a (\pi a^3) \in_0 K_1 (K_2 - K_1)/(K_2 + K_1) \nabla |E_0|^2 \qquad \text{Equation 2}$$

Where:

F is the dielectrophoresis force vector detected by the antenna and the device's other component parts;

a is the radius of the sphere or cylinder;

L is the length of the cylinder (L/a is the so-called axial ratio);

$\in_0$ is the permittivity constant of free space;

$K_2$ is the dielectric constant of the material in the sphere or cylinder;

$K_1$ is the dielectric constant of fluid or gas, (air) surrounding both the entity and the antenna and the device's other component parts;

$E_0$ is the electric field produced by the entity as detected by the antenna and the device's other component parts; and $\nabla$ is the spatial gradient mathematical operator.

It should be noted that the term "antenna" as used in this context includes (in a very real sense) all of the components present in the device of the present invention, including the living human operator. To this extent, the dielectric constant of the materials that make up the locator and the living human operator of the present invention all determine the overall value of $K_2$ in the above equations. These materials are not arranged in a uniform spherical or cylindrical shape, and therefore the exact value of $K_2$ and the functional relationship of $K_2$ to $K_1$ are difficult, if not impossible, to determine in a closed form of a mathematical equation. In a practical sense, experimentation has shown (and is continuing to show) the types and placement of dielectric materials needed to produce a maximum dielectrophoretic force and subsequent resulting torque, acceleration, vibration or any other measurable quantifiable manifestations of the force for precisely locating different types of entities. The following table lists some of the dielectric materials possibly used in the locator ($K_2$ values) and/or surrounding (such as air, water, walls, etc.) the locator ($K_1$ values) and the dielectric constant for these materials.

| MATERIAL | DIELECTRIC CONSTANT |
|---|---|
| air | 1.0 |
| PVC | 3.0 |
| nylon | 4.0 |
| polyester | 5.5 |
| silicon | 12.0 |
| 2-propanol | 19.9 |
| water | 78.4 |
| n-maa | 191.3 |
| selenium | 1000 |
| BaTiO$_3$ | 4000 |
| (CS$_2$)$_n$ | 20,000 |
| metal | $\infty$ |
| lung | $3 \times 10^7$ |

-continued

| MATERIAL | DIELECTRIC CONSTANT |
|---|---|
| heart muscle | $7 \times 10^6$ |
| skeletal muscle | $1 \times 10^7$ |
| liver | $5 \times 10^7$ |
| fat (100 Hz) | $2 \times 10^5$ |
| kidney (10 kHz) | $5 \times 10^4$ |
| blood (10 kHz) | $3 \times 10^3$ |
| brain (100 kHz) | $4 \times 10^3$ |
| bone (100 Hz) | $4 \times 10^3$ |

The above discussion and equations concerning dielectrophoresis provide a rational explanation of the operating principles of the present invention that is consistent with all empirical observations associated with the present invention. These operating principles involve using the above-mentioned forces to point an antenna toward the maximum spatial gradient of the local electric field, to thereby indicate the direction toward an unseen entity.

In accordance with the invention, an operator holds the locator device in hand, and through a handle, the locator device is electrically connected to the operator. The operator is partially electrically grounded (through the operator's feet), and thereby the individual human operator body's capacitance (C) and resistance (R) to true ground are connected electrically to the handle of the locator device. Ranges for individual human body's C have been measured as 100 pF to 400 pF and for individual human body's R have been measured as 0.03 KΩ to 1 MΩ. Thus, the generalized electrical parameter (the polarization charge pattern induced on the device by the electric field spatial gradient of the entity in this case, but also electric field, current and voltage) exponential decay time (=RC) constant range for the variety of human being bodies potentially acting as locator device operators is about 3 to 400 $\mu$ seconds. This decay time constant is greatly increased through an externally connected series resistor of up to 100 KΩ and parallel capacitor up to 0.01 mF, which results in an effective human operator's exponential decay time constant up to 1 to 10 seconds.

This enables dielectrophoretic forces caused by the induced polarization charge pattern on the locator device antenna and other component parts to be detected, replenished instantly and locked onto since the force is replenished faster than the induced polarization charge pattern on the device can decay away to true ground through the operator's body. This effect is called, and is using, the spatially self-correcting nature of the dielectrophoretic force (always pointing or trying to point to the maximum of an entity's electric field three-dimensional squared spatial gradient pattern, which in the case of inanimate entities, is static electrification induced.

The locator device is held in a balanced, few degrees down tilt from the exactly horizontal state, and the operator scans the locator device in a constant speed uniform linear motion back and forth. An antenna extends from the front of the locator device and is acted on along with the device's other components by the aforementioned forces. These forces create a subsequent resulting torque around a well defined pivot line which tends to make the locator device's antenna and the device's other component parts point toward the maximum spatial gradient of the square of the non-uniform electric field uniquely exhibited by any target entity within the range of the locator device.

Four internal N-channel J-FETs (field effect transistors) are connected to the locator device's antenna and operate in their non-linear range to effectively change the antenna's length. Three of these FETs are arranged in modules that are equidistant from the antenna's longitudinal axis and are spaced 120° apart. The fourth FET is arranged in a module below the axis and to the rear of the locator device. Three potentiometers are provided on the first three modules to adjust the current levels through the first three FETs and thereby tune the locator. The gain and frequency response of the fourth FET is adjusted by a six position switch connected to the base of an NPN transistor. By changing the frequency response of the locator device, the device is tuned to reject the higher frequency electromagnetic signals and noise from all external sources, including those sources associated with the human operator himself in order for the locator device to interact with and respond to only the three-dimensional non-uniform electric field squared spatial gradient pattern exhibited uniquely by a predetermined entity type.

While scanning the locator device in a constant speed uniform linear motion back and forth in front of a known or reference entity, the operator changes the six position switch until a maximum force and subsequent resulting torque is detected and used to aim the antenna and the device's other component parts toward the target entity. After selecting the setting of the six position switch, the operator adjusts the gain of the first three FETs until the locator device points or tries to point directly at the target entity. For different entities, different dielectric materials are used for the antenna and other component parts. Examples of detectable entities include metals, plastics, polymers and other inanimate materials. Continued research on the instrument has yielded positive results in the instrument's ability to be tailored both as a geometrical design and with respect to materials of construction to specifically detect a variety of different target entities. Accordingly, it is an objective of the invention to provide an accurate method of locating the direction and position of target entities relative to a human operator. It is another objective of the invention to provide improved elements and arrangements thereof in an apparatus for the purposes described which is inexpensive, dependable and fully effective in accomplishing its intended purposes.

BRIEF DESCRIPTION OF THE DRAWINGS

These and other objectives of the present invention will become readily apparent upon further review of the following specification and drawings, wherein.

DETAILED DESCRIPTION OF PREFERRED EMBODIMENTS

Figure 1:
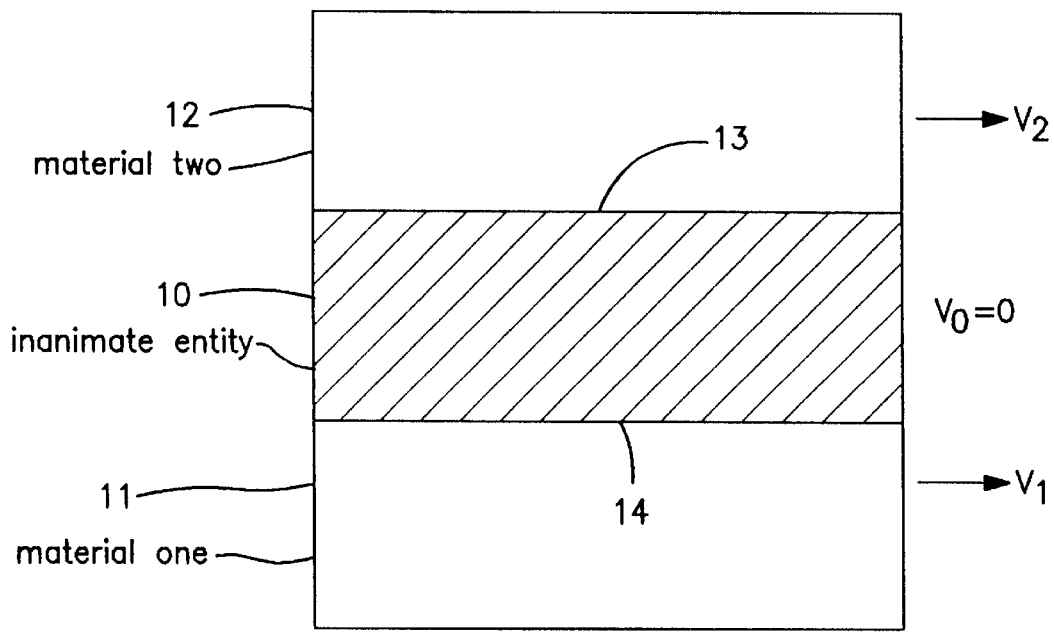
FIG. 1 is a schematic of static electrification of an inanimate entity.
Figure 6:
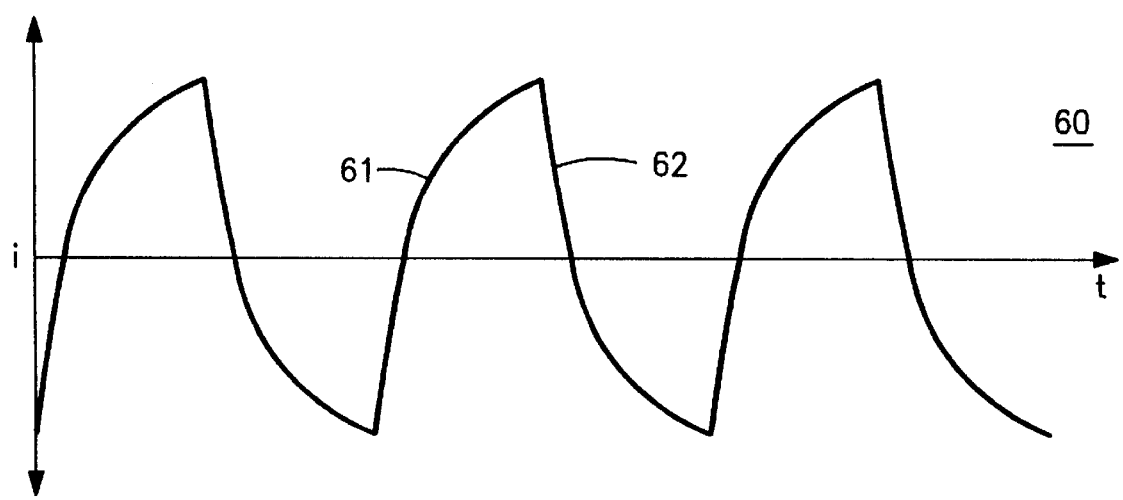
FIG. 6 shows ideal ULF waveform for repeated charge/discharge cycles due to static electrification and de-electrification of an entity surface.
Figure 2:
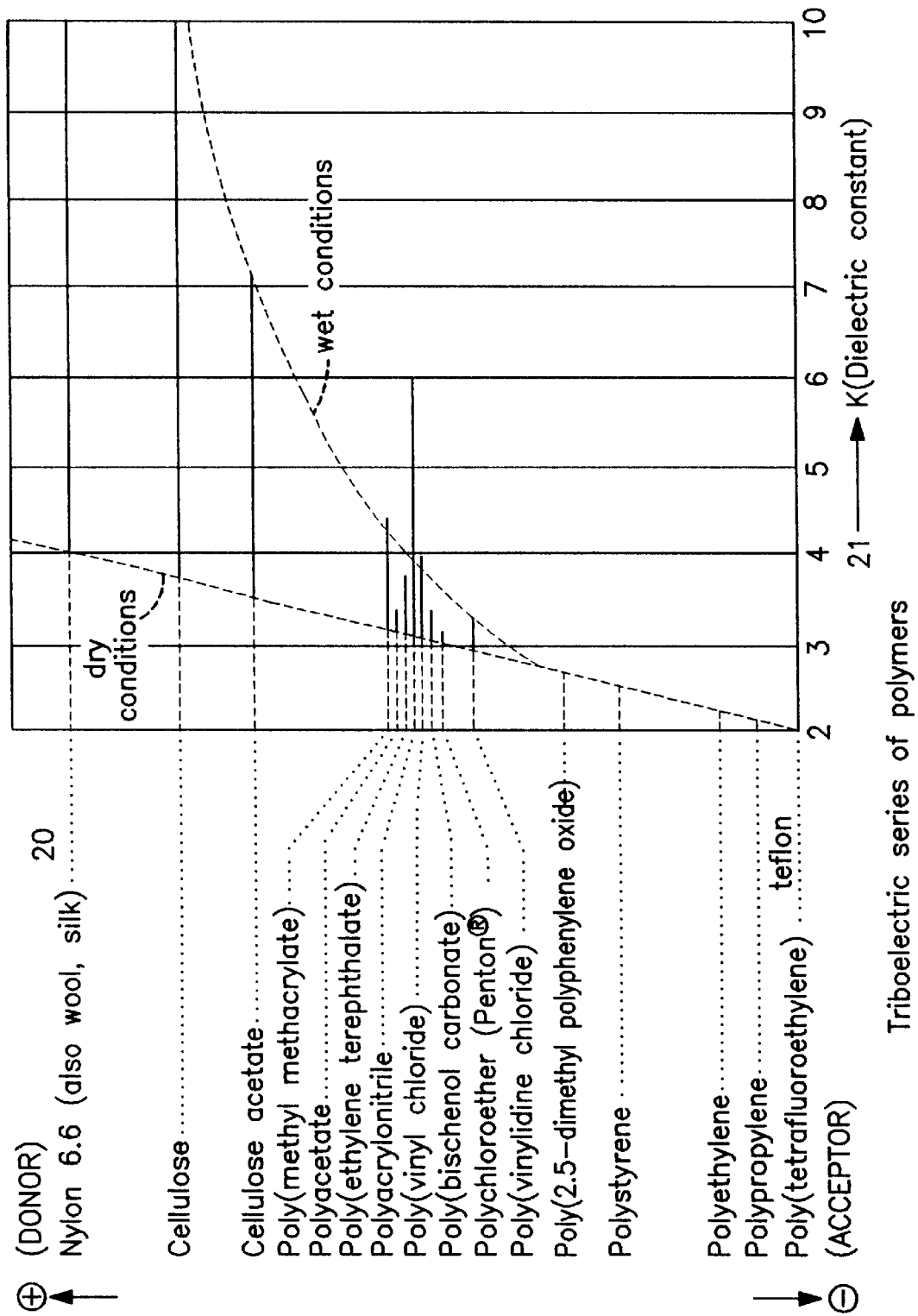
FIG. 2 shows the triboelectric series of polymers versus dielectric constant.
Figure 3:
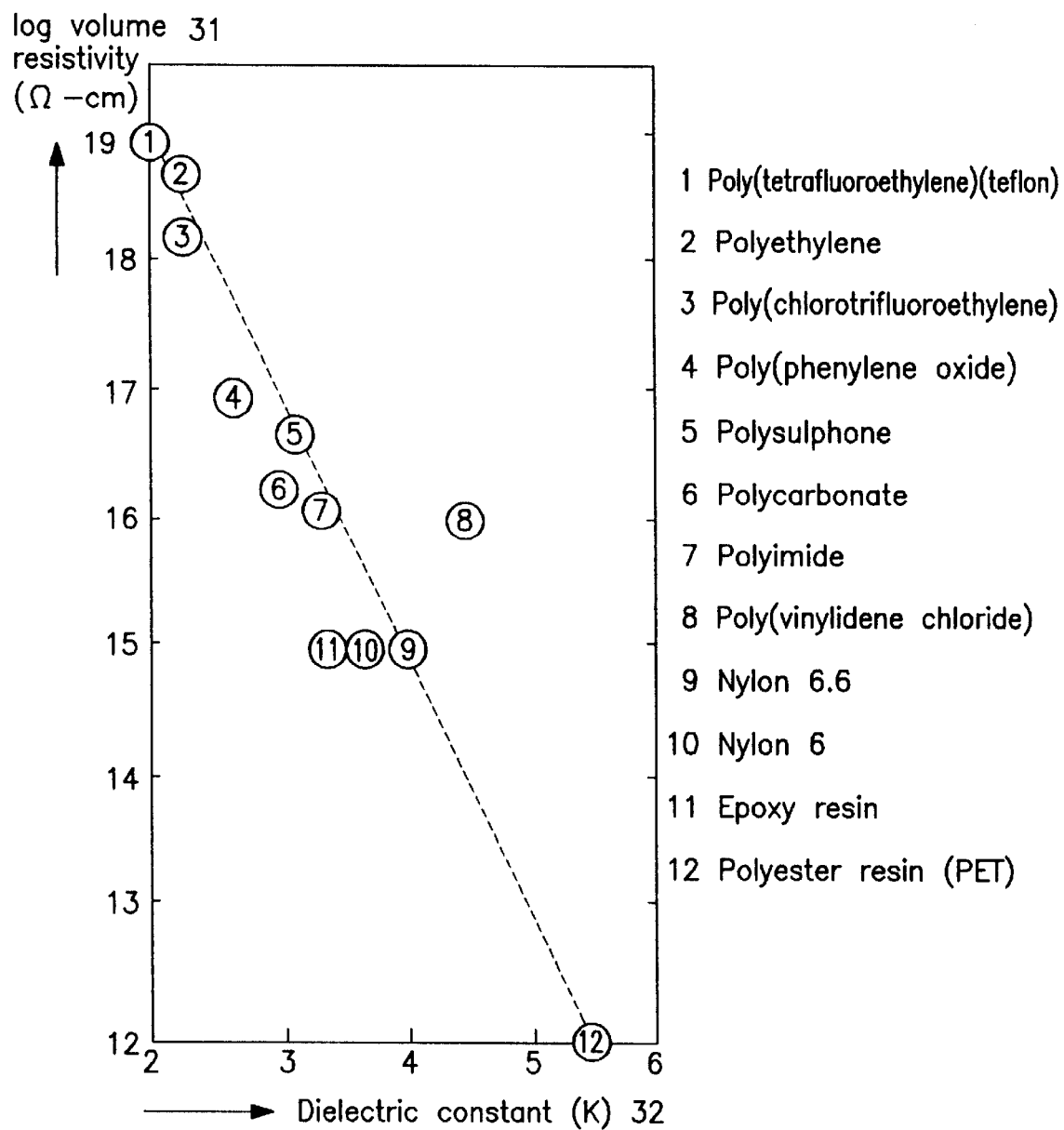
FIG. 3 shows the correlation between bulk electrical resistivity ρ and dielectric constant K.
Figure 4:
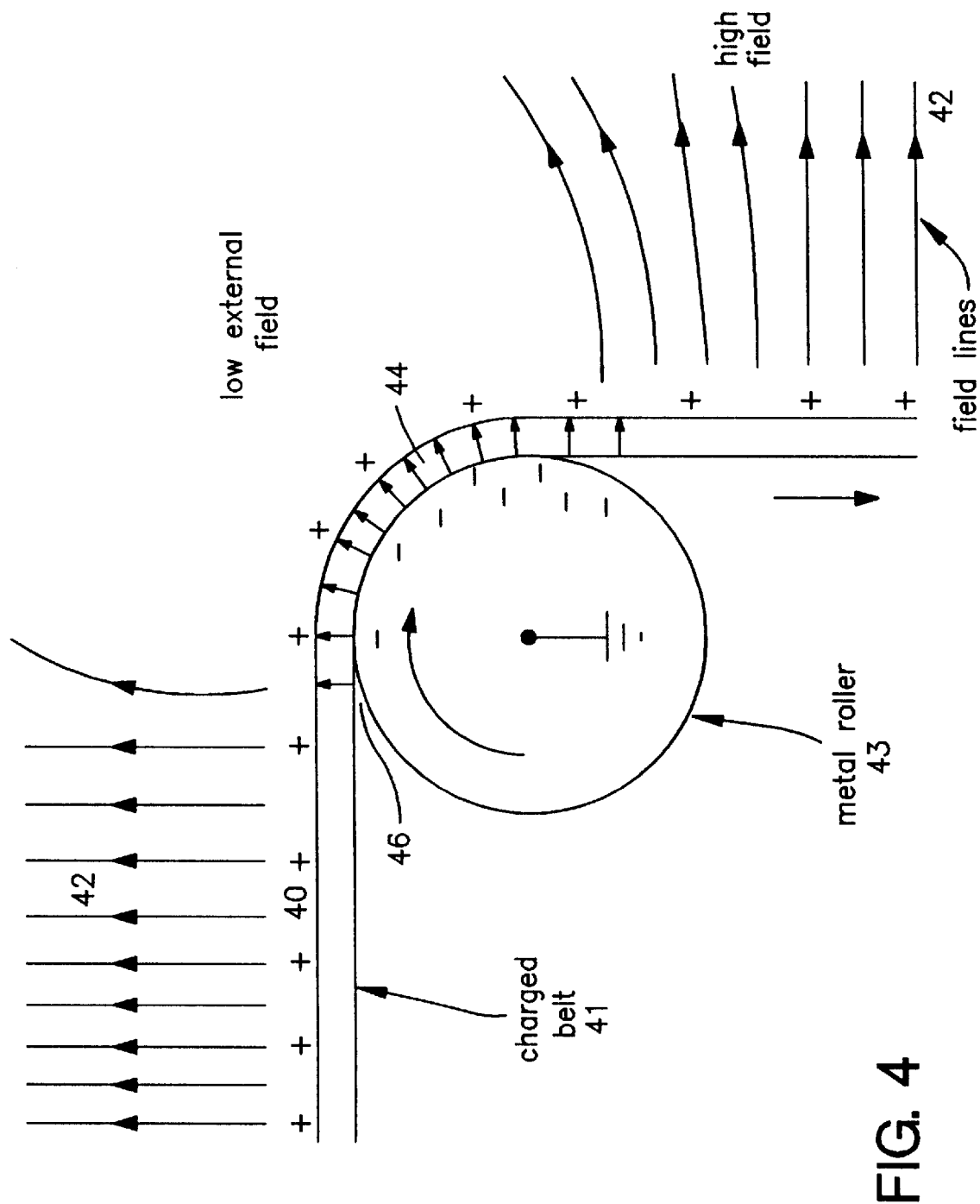
FIG. 4 shows static electrification electric field spatial gradient where a charge polymer web moves in contact over a grounded metal roller.
Figure 5A:
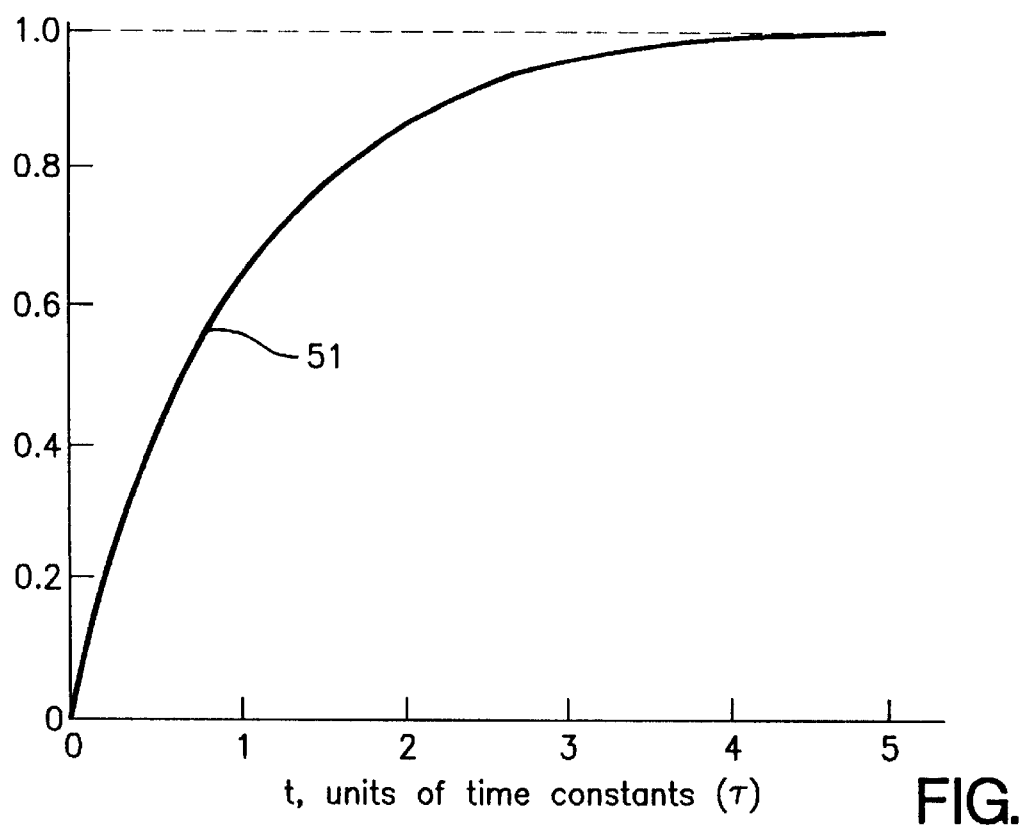
FIGS. 5(a) and (b) show the exponential growth and decay curves for surface voltage, electric fields and spatial gradients from static electrification.
Figure 5B:
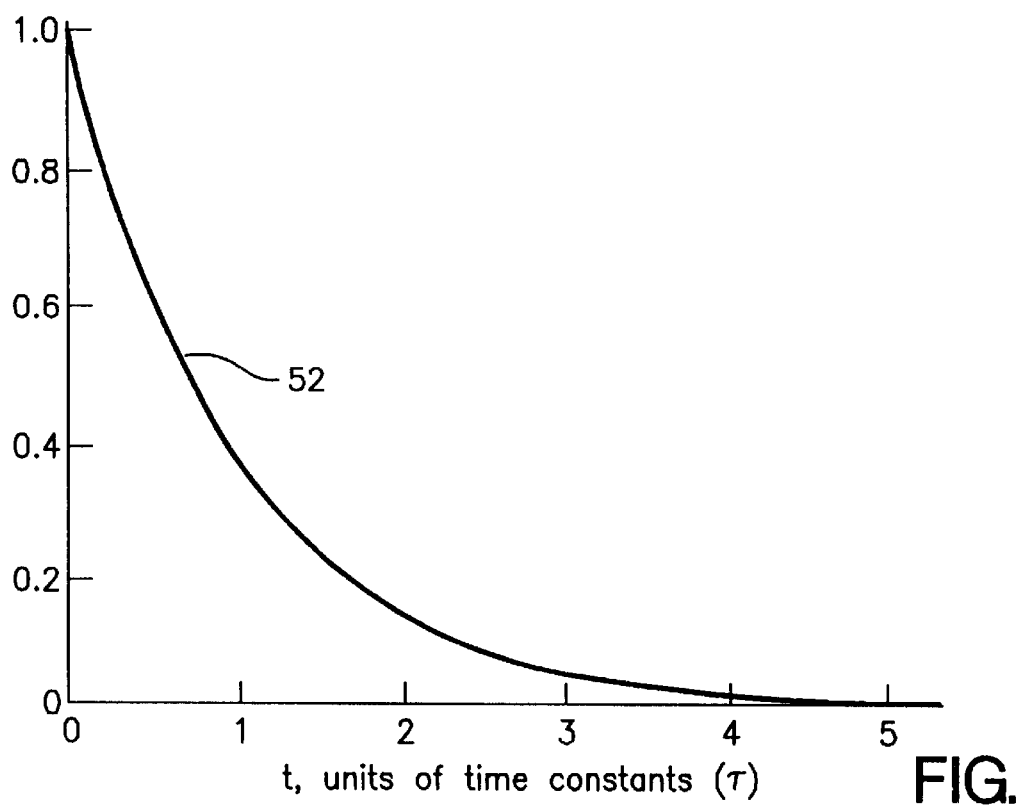
Figure 7:
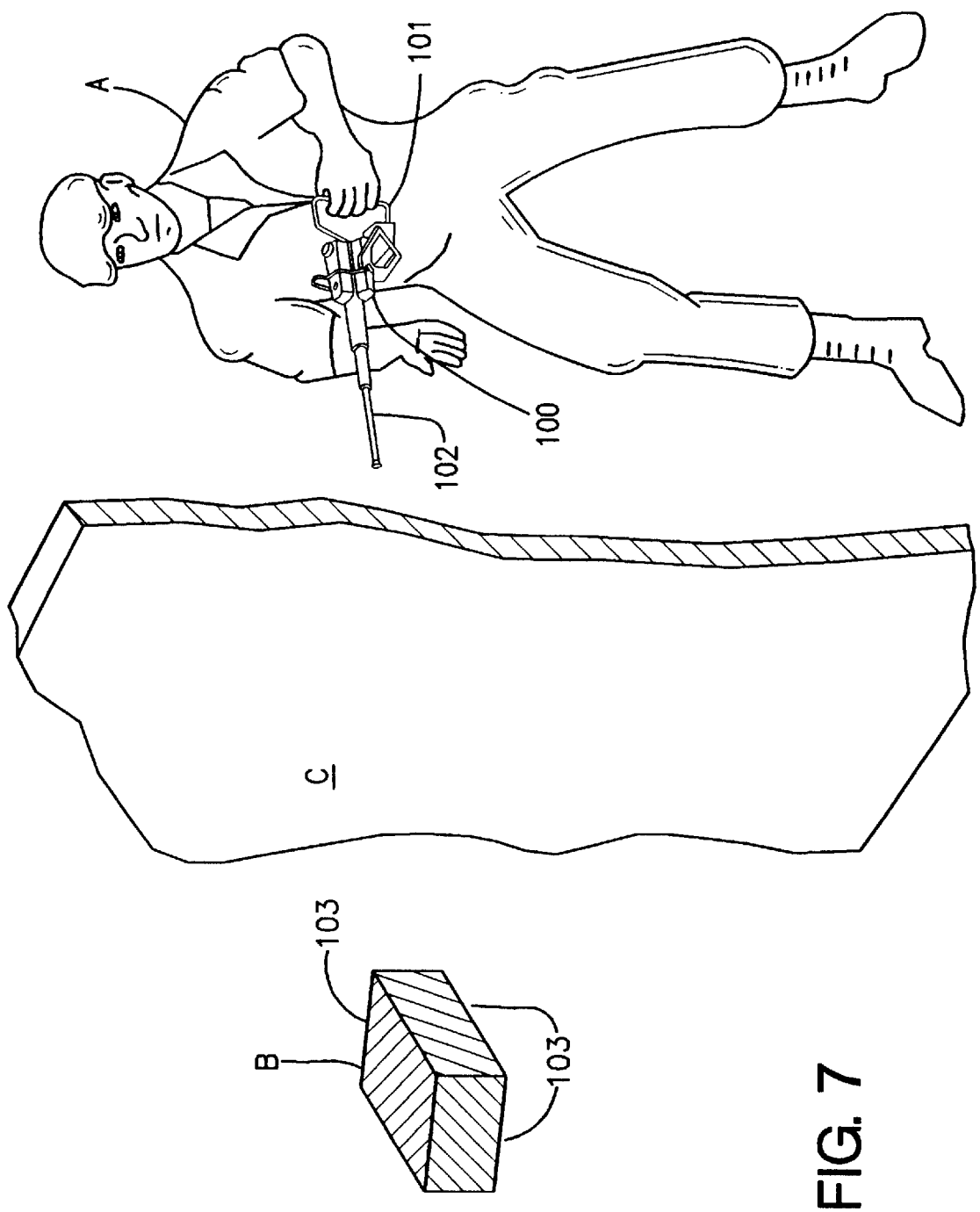
FIG. 7 shows a human-operated, hand-held line-of-bearing locator locked-onto the inanmate entity even through a vision-obscuring barrier.

The device according to the present invention is shown as locator device 100 in FIG. 7. FIG. 7 shows a human operator A using such a locator device 100 as it rotates about hand-held pivot line 101 as antenna 102 responds via dielectrophoresis and points to the largest electric field spatial gradient on the surface of the inanimate entity's B surface 103. The electric field lines and gradients are partially directionally distorted and focused toward the human operator A due to the operator's extraordinarily high dielectric constant at ULF, hence increasing the sensitivity of the locator device 100 despite a vision-obscuring barrier material C.

The human operated hand-held locator device produces an observable torque as the device swings around the hand-held pivot point and acquires a local electric field spatial gradient maximum which gives, via the dielectrophoresis force, a pinpoint line-of-bearing location of the target inanimate entity. The location detector specifiously locates the maximum electric field spatial gradient on the entity surface produced by static electrification. The size and extent of the observable torque depends on the angular, radial and vertical planar positions of the human operator. Despite inanimate entity target movements, the detector is directionally self-correcting, it reacquires in real time and "locks-on" to the spatial gradient signal and again pinpoints the electric field spatial gradient maximum of the inanimate entity. At sub-ULF and ULF frequencies utilized in the static electrification of inanimate entity surfaces, attenuation "skin" depths are extraordinarily large, so the detector can operate through metals, earth, walls, and all other vision-obstructing barriers.

Figure 8:
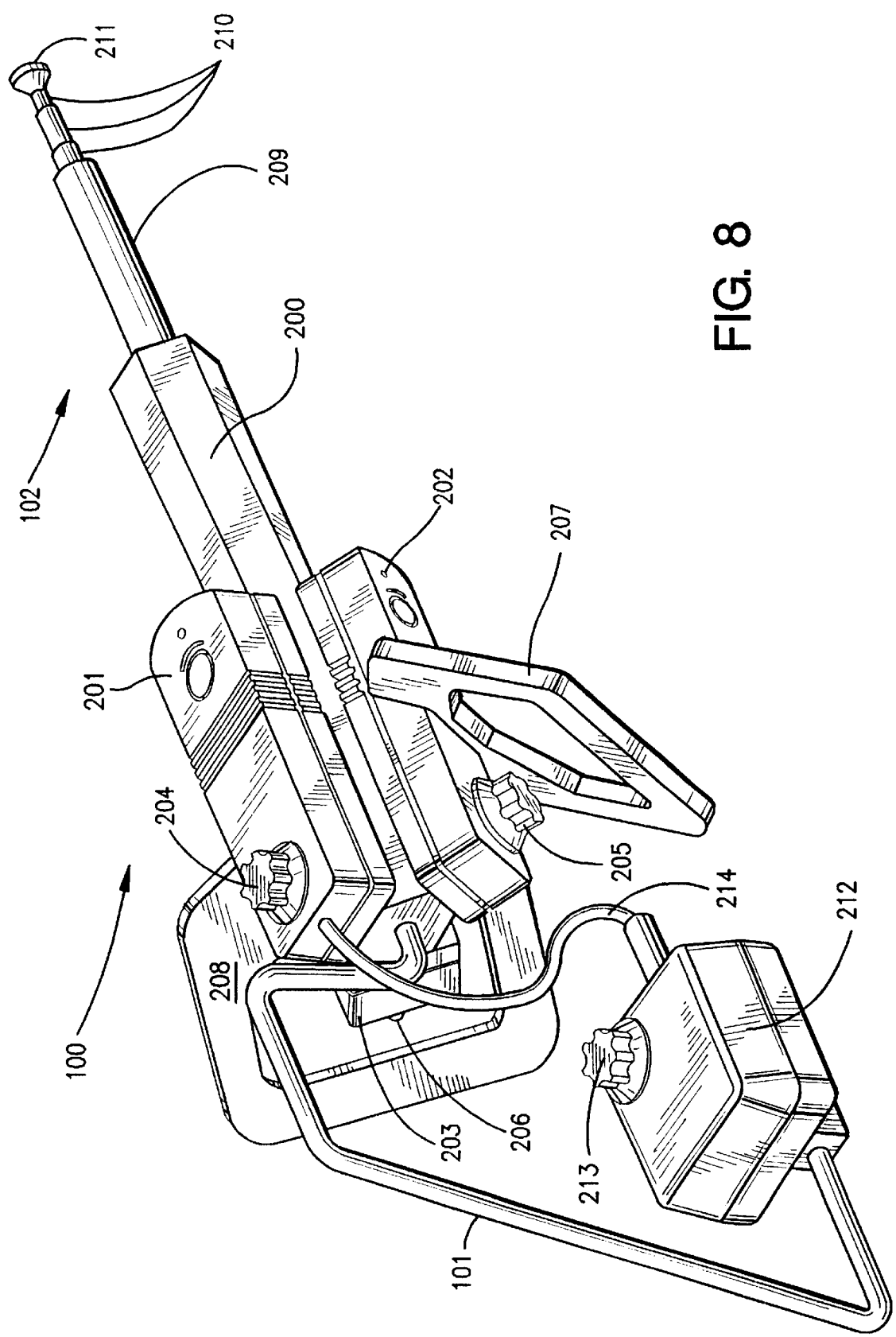
FIG. 8 is a perspective view of the locating device in accordance with the present invention.
Figure 9:
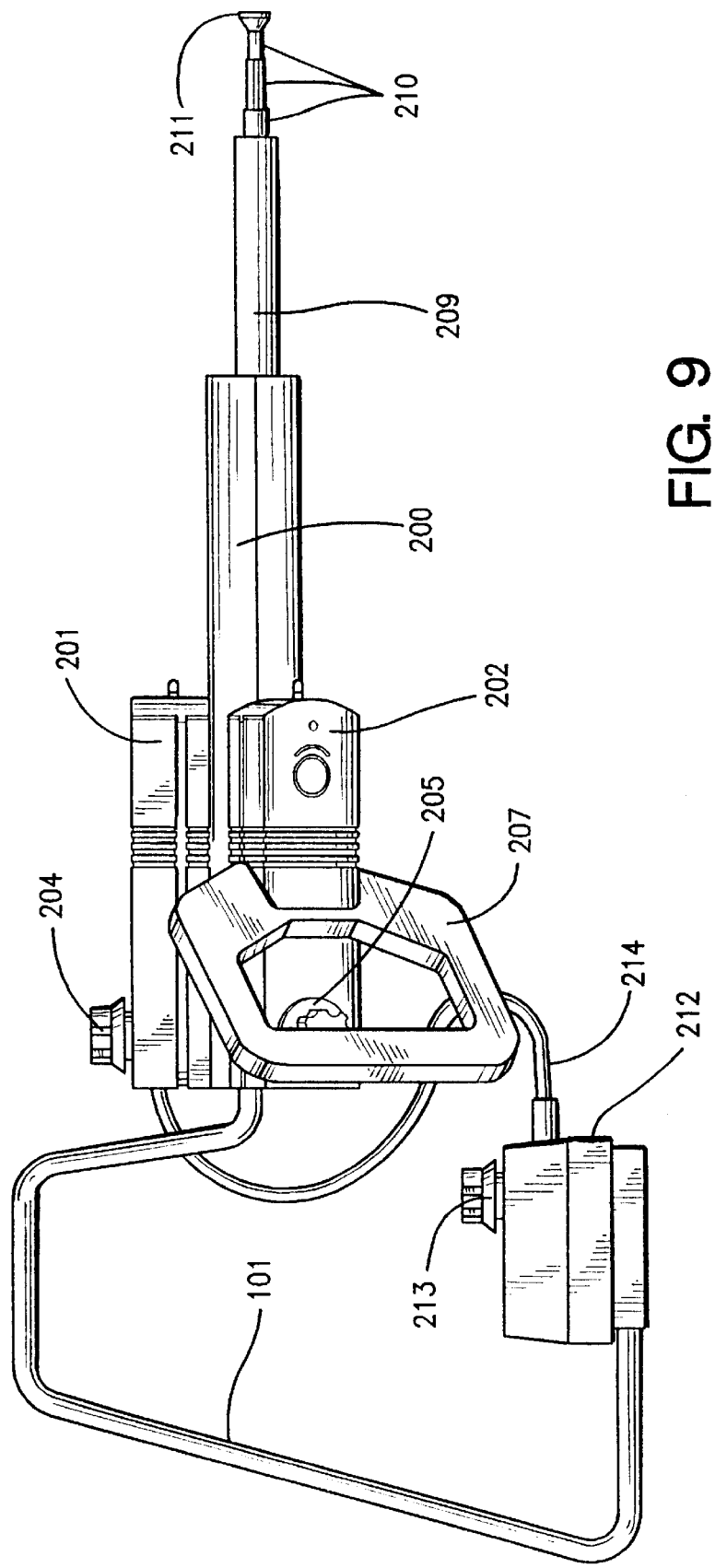
FIG. 9 is a right side view of the locating device shown in FIG. 8.
Figure 10:
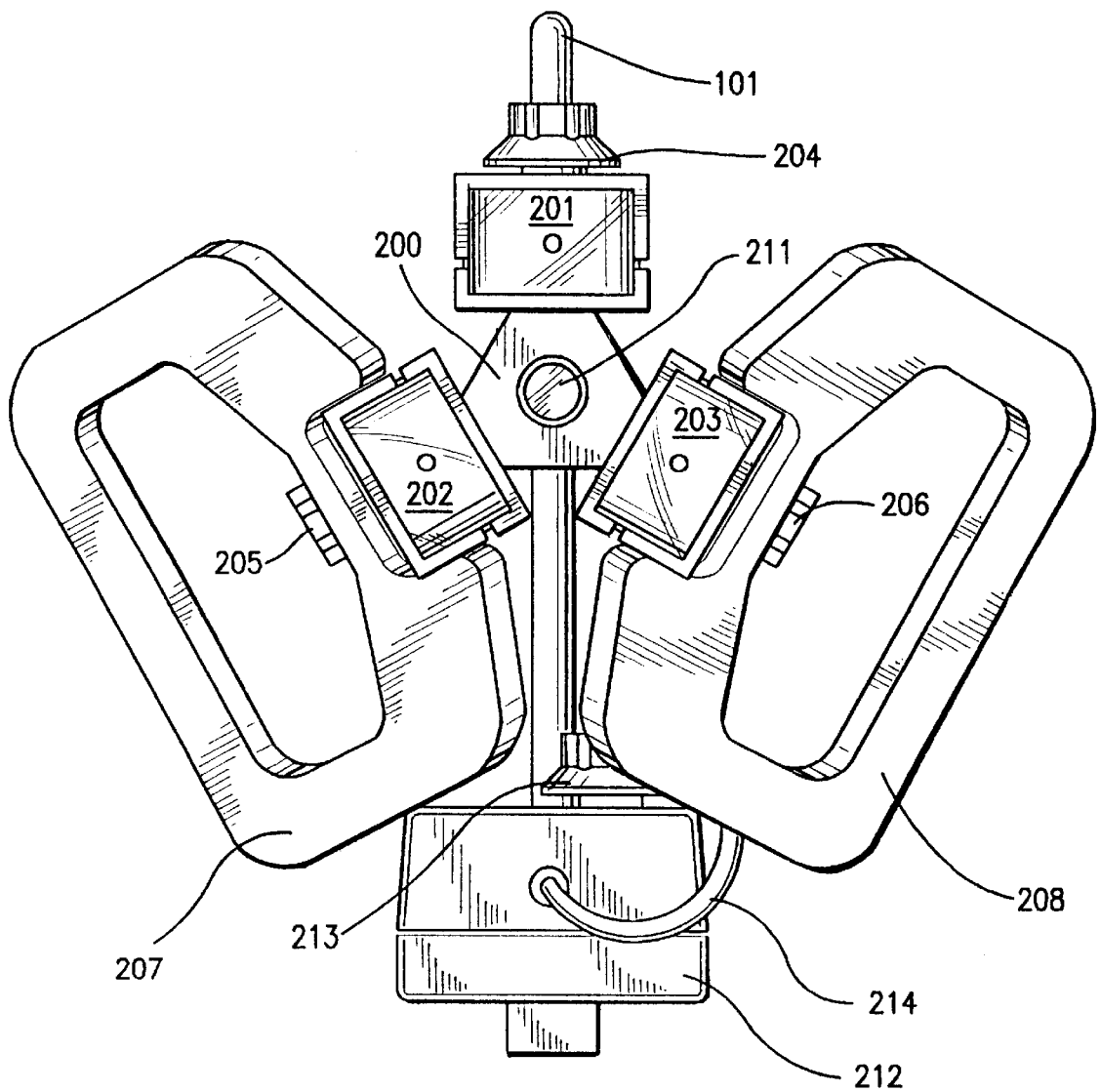
FIG. 10 is a front view of the locating device shown in FIG. 8.

The details of the exterior of the locator 100 can be seen in FIGS. 8–10. The antenna 102 includes a rear portion 209 made of nylon or similar material, telescoping sections 210, and an end knob 211. The antenna 102 protrudes from a central dielectric housing 200 in a coaxial arrangement. The antenna telescoping sections 210 and the antenna rear portion 209 can be moved singly or jointly to adjust the axial ratio of the locating device 100 to obtain optimum torque-induced pivoting response of the locator 100. The enhancement is obtained by changing the length of the antenna and/or changing the exact relative position of the whole antenna compared to the positions of the other device components. The antenna 102 does not necessarily have to be of the telescoping type, nor made of metal material and can be a one piece rigid or flexible type antenna made from metal or plastic materials. Furthermore, as all of the components of the locator device 100 effectively act as an antenna, the locating device operates as described without the antenna 102 installed, although the forces produced are greatly reduced.

Attached to the central dielectric housing 200 are three modules 201, 202, 203. The top module 201 is mounted directly over the common axis of the antenna 102 and the central dielectric housing 200 and in line with this axis. The lower right module 202 and lower left module 203 are spaced 120° apart from each other and the top module 201 and are also in line with the axis. Each module 201, 202 and 203 has a variable resistor control knob 204, 205 and 206, respectively. The lower right module 202 and lower left module 203 include parabolic antennas 207 and 208, respectively, both of the parabolic antennas being attached to their respective module in a swept back position. The handle 101 is formed from a metal rod that protrudes coaxially from the central dielectric housing 200. The handle 101 bends upward, extends horizontally for a short distance, bends downward to form a handle, and then bends forward to provide a support for a bottom tuning module 212. The bottom tuning module 212 includes a variable resistor control knob 213 and a cable 214 that attaches to the top module 201.

Figure 11:
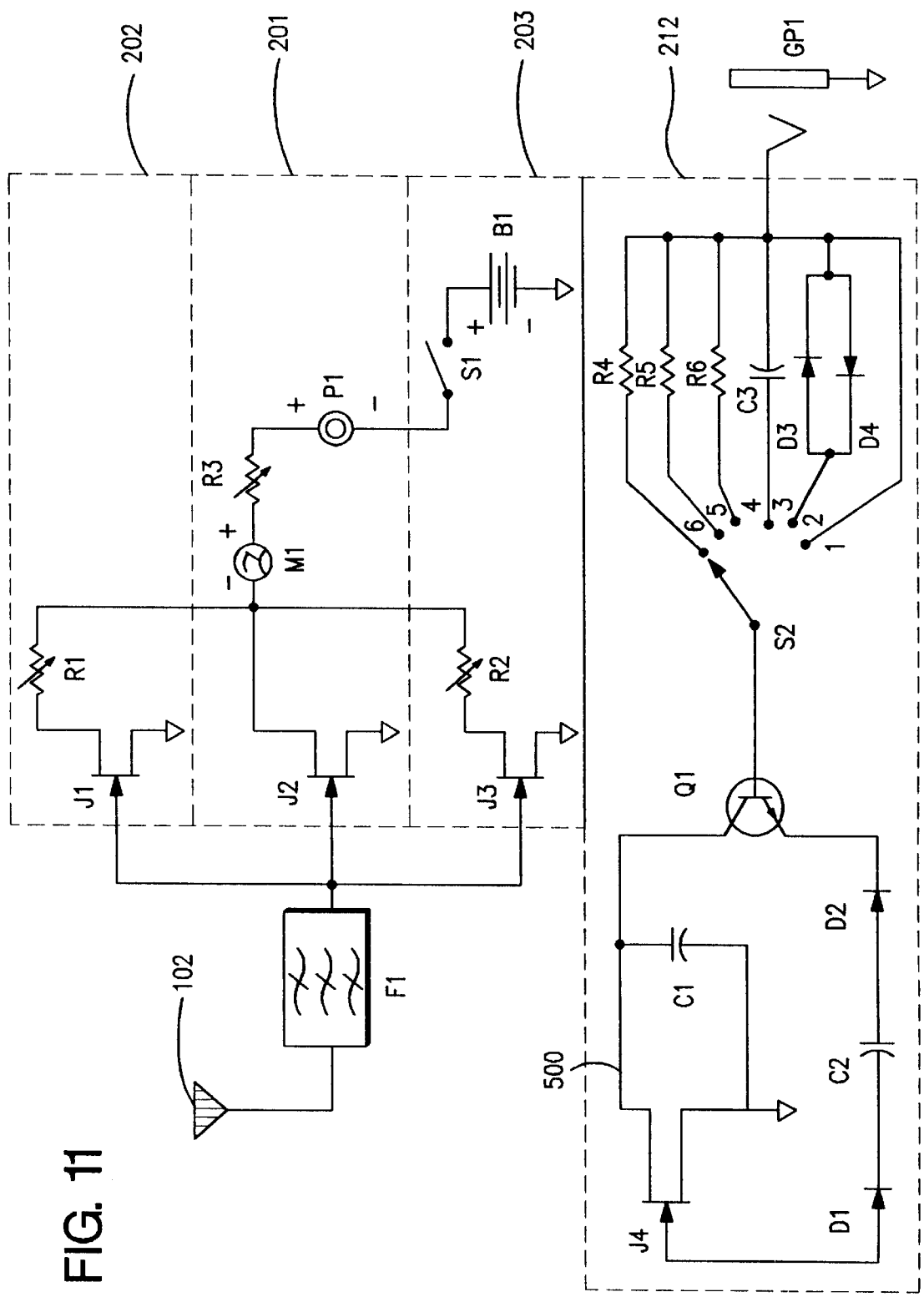
FIG. 11 is a schematic diagram of the three main modules and the bottom tuning module of the locating device of FIG. 8.

The electronic circuitry for the locator device 100 is shown in FIG. 11. The antenna 102 is connected to an optimal low pass filter F1, which removes all high frequency signals and noise from all external electromagnetic sources, including those from the human operator A himself. The details of the electronic circuitry and the geometrical design and materials of construction used in the locator device 100 are chosen so as to tailor the locator device 100 for a predetermined entity type. The output from the optimal low-pass filter F1 is fed to the gate of the three N-channel field effect transistors, (FETs). The three FETs act as amplifiers and are housed one each in the three modules. The lower right module 202 contains FET J1 and a 0–100 k$\Omega$ variable resistor R1, the top module 201 contains FET J2, a DC ammeter M1, a 0–100 k$\Omega$ variable resistor R3, and a piezo buzzer P1, and the lower left module 203 contains FET J3, a 0–100 k$\Omega$ variable resistor R2, an on/off switch S1 and a 9-volt battery B1.

Variable resistors R1 and R2 adjust the current gain of FETs J1 and J3, respectively. By adjusting the gain of these FETs, the effective electrostatic effect on these devices is balanced relative to FET J2. The overall gain of FETs J1, J2 and J3, is adjusted by 0–100 k$\Omega$ variable resistor R3. The DC ammeter M1 is provided to indicate the combined current flow through all three FETs. In addition, the piezo buzzer P1 provides an audio output whose frequency increases as the current through the circuit increases. The battery B1 provides the required supply voltage (preferably nine volts) to operate the circuit, and the switch S1 provides a means for turning the amplifiers J1–J3 on and off.

The bottom module 212 contains the necessary circuitry for increasing the human operator's electrical parameter decay (RC) time constant, from $\mu$ seconds as occurs naturally to seconds as explained previously, needed to capture and lock onto the dielectrophoretic force exhibited by a target inanimate entity and the subsequent resulting torque, acceleration, vibration or any other measurable, quantifiable manifestation of the force detected by the locator device 100. A ⅛ inch grounding jack GP1 is used to provide a ground to the circuit by inserting a mating shorting plug into the jack GP1. Once inserted, the mating plug (via the jack GP1) provides a ground potential via the reference entity RE to each of 3.3 k$\Omega$ resistor R4, 22 k$\Omega$ resistor R5, 100 k$\Omega$ resistor R6, 0.01 mF capacitor C3, clipping diodes D3 and D4, and position one of a six-position selector switch S2. The six-position selector switch S2 can be moved to one of six positions to connect the base of an NPN transistor Q1 to one of the above components. The NPN transistor Q1 makes up part of a tunable circuit that also includes an N-channel FET J4, a first 0.01 μF capacitor C1, a first diode D1, a second diode D2, an electrical line 500, and a second 0.01 μF capacitor C2. By inserting or removing the shorting plug into the jack GP1 and changing the position of the switch S2, the gain of the transistor Q1 can be adjusted, and the overall frequency response of the tuned circuit in the bottom module 212 can be changed for maximum response. The extraordinarily high ULF dielectric constants for living tissues, given in the previous table, allows the human operator's electrically grounded body to directionally distort, concentrate or focus the non-uniform electric field pattern emanating from the inanimate entity target. This action greatly increases the electric field flux density near the locator device. This field line concentrating increases the torque-producing dielectrophoresis force and results in an effective increase in the amplification or gain of the locator device as the human operator samples the electric flux density as the device is moved in a uniform constant speed linear motion back and forth to initiate torque and lock-on.

The torque-produced pivoting response can be further increased by adding additional circuit elements such as capacitors, resistors and/or inductors to the circuit already described with reference to FIG. 11. These circuit elements decrease the response time of the locator device. Preferred value ranges for the elements are up to 56 mF for the capacitors, up to 5,000 MΩ for the resistors and up to 200 mH for the inductors. These circuit elements serve to modify and optimize the device's polarization response and decay time constants.

As stated earlier, all of the components in FIG. 11 act as antenna extensions that increase the dielectrophoretic force and the subsequent resulting torque that is detected by the locator device 100. Every human being, as a locator device operator, has a different capacitance (C) and resistance (R) resulting in a low exponential decay time constant (=RC) for capturing and locking onto the dielectrophoretic force and the subsequent resulting torque. By adjusting R1–R3 and S2, the individual human operator and the locator device 100 can be jointly tuned and optimized to detect the maximum dielectrophoretic force and subsequent resulting torque for the specific human being operating the locator device 100. This is accomplished by using a reference entity (such as a visible entity) and adjusting S2 and R3 until the maximum dielectrophoretic force and subsequent resulting torque are detected by the individual human operator. Once the position of S2 has been determined, the operator notes the direction the antenna is pulled relative to the reference entity. If this direction is not exactly toward the reference, R1 and R2 are adjusted until the torque on the locator device 100 tends to point the antenna 102 directly toward the reference entity. After the locator device 100 is tuned and optimized, unobserved entities can be easily located by the device.

Figure 12:
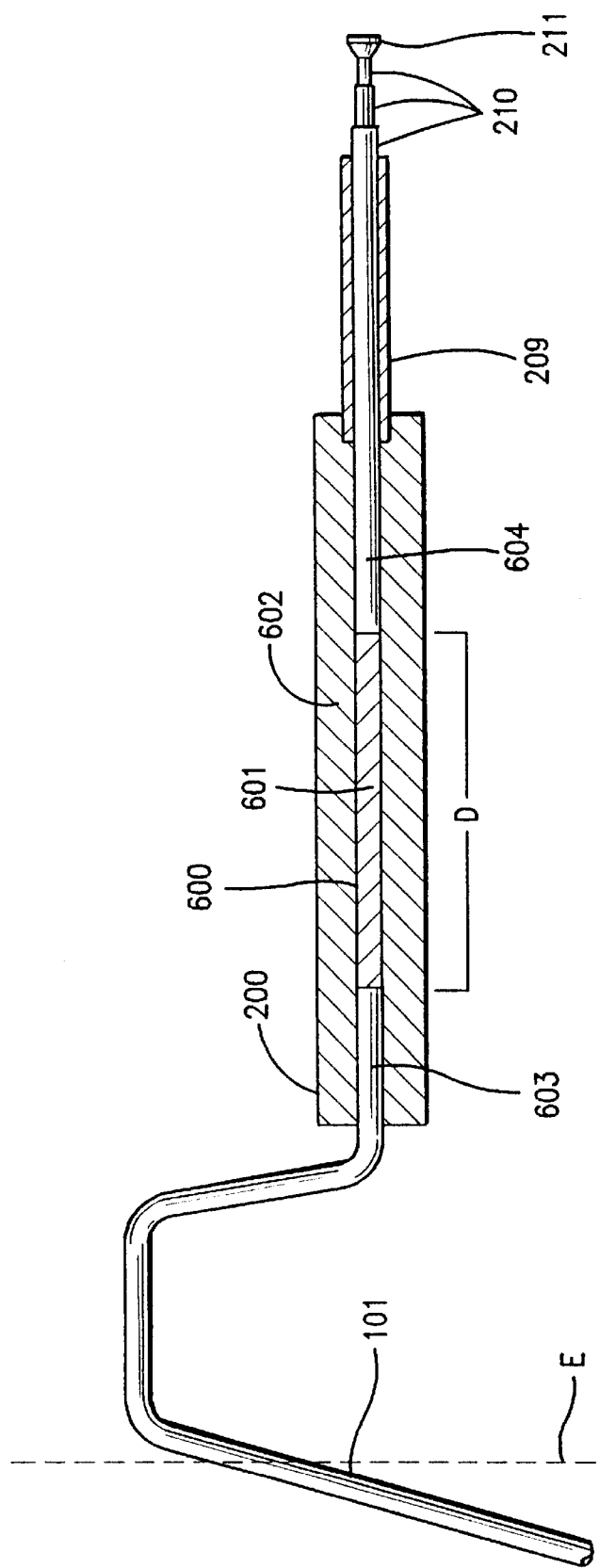
FIG. 12 is a cross-sectional view along the length and through the center of the locating device of FIG. 8.
Figure 13:
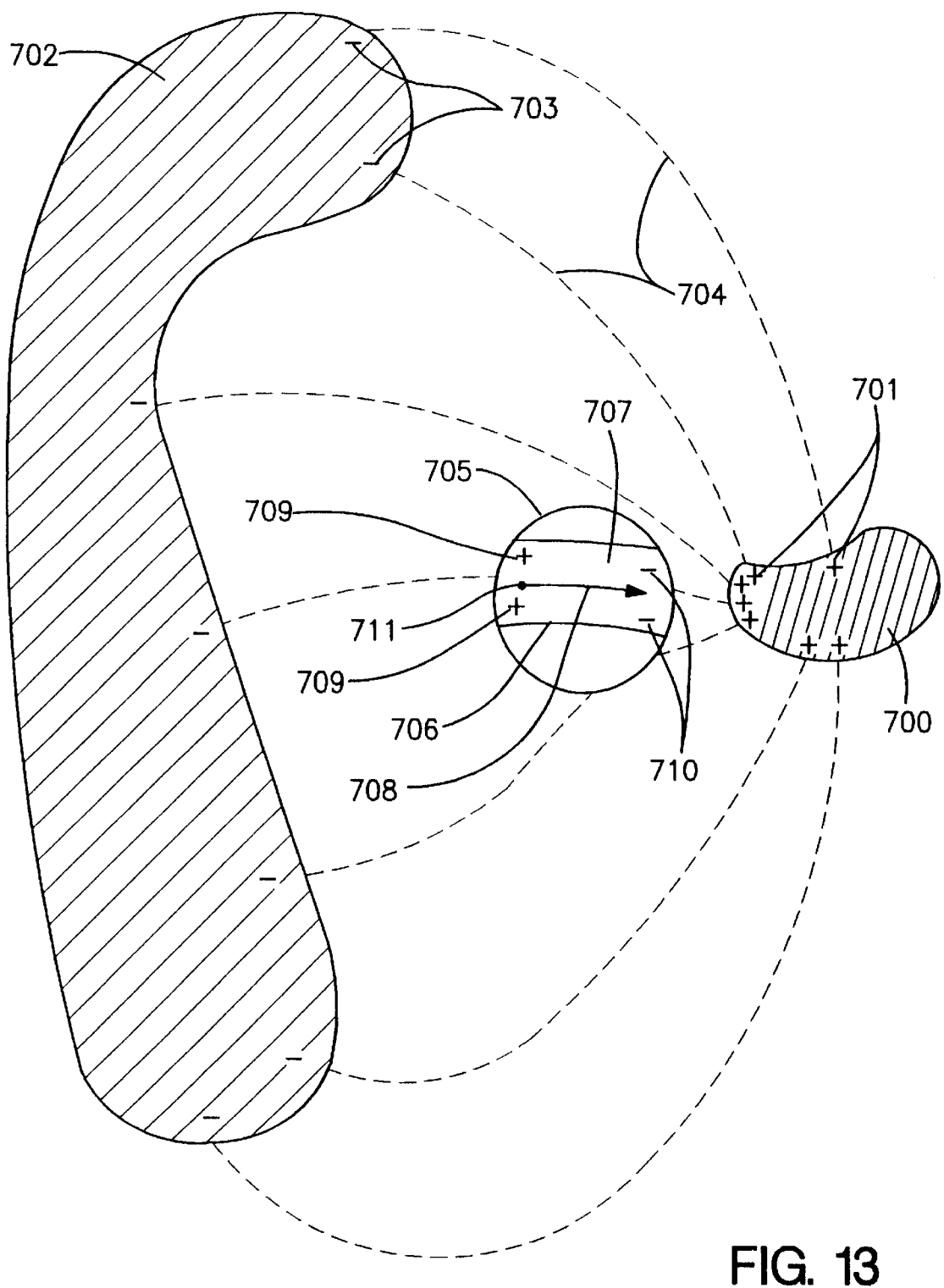
FIG. 13 is a schematic drawing of an entity, a ground plane, the device of the present invention and the entity's polarization electric field lines.

The interior of the central dielectric housing 200 is shown in FIG. 12. One end 604 of the telescoping antenna 210 extends into the front end of the housing 200, while an end 603 of the handle 101 extends into the rear end of the housing 200. A cavity 600 is filed with a first dielectric material 601 that surrounds both the interior end 604 of the telescoping antenna 210 as well as the interior end 603 of the handle 101. Around this cavity 600 is a second dielectric material 602 that defines the shape of the cavity 600 and also contacts the interior end 604 of the telescoping antenna 210 as well as the interior end 603 of the handle 101 near the point where end 604 and end 603 exit the housing 200. The device's handle 101 with the operator's hand defines a pivot line E around which the dielectrophoretic force produces the subsequent resulting torque, acceleration, vibration or any other measurable, quantifiable manifestation of the force. The ends 604 and 603 are separated by a distance D, which distance is human-operator-specific and also affects the overall sensitivity and response of the locator device 100 with respect to maximum detectable force and torque.

While the specific dielectric materials for maximizing the torque effect on the antenna for different entities are still being researched, dielectrics have been found that produce a usable torque for precisely locating inanimate entities. In particular, the handle 101 and the antenna 102 preferably contain some metal, material 601 is air, material 602 is PVC, and the rear portion 209 of the antenna is nylon. In addition, the circuitry in modules 201, 202, 203 and bottom module 212 is encapsulated in PVC, while the modules themselves, housing 200, as well as the parabolic antennas 207 and 208, are also made of PVC. When these materials are used, an effective dielectrophoretic force and the subsequent resulting torque are detected by the antenna 102 and the device's other component parts to precisely locate the presence of inanimate entities. Dielectric material 601 may alternately be selected from the following materials with varying levels of resulting torque: water (distilled, deionized), glycerol, (di)ethylene, triethylene glycol, 2-ethyl-1,3-hexanediol, γ-butyrolactone, dimethylpropionamide, di-methyl sulfoxide, methanol, ethanol, 2-propanol, 2-propyl-2 methanol, PVC, ABS, etc., or any one of several well-known engineering plastics, barium titanate, lead titanate, and lead zirconate titanate. Device housing material 602 can be made from polyvinyl chloride, polyurethane, or any one or more of well-known engineering plastics.

FIG. 12 shows a target entity of interest 700 and a surrounding ground plane 702. The entity's polarization charges 701 produce non-uniform electric field lines 704 that have a unique spatial pattern as shown. The non-uniform electric field lines 704 also have a unique spatial gradient pattern (not shown). The non-uniform electric field lines 704 terminate on the surrounding ground plane 702 and induce opposite polarization charges 703 thereon. An initially neutral matter or medium 705, such as the device of the present invention, is shown amidst the non-uniform electric field lines. The neutral matter 705 includes a cavity 706 filled with a specific dielectric material 707. The non-uniform electric field lines induce polarization charges 709 and 710 in the dielectric material 707. The neutral matter 705 also contains protuberant antennas 708 that are formed from a specific dielectric material and are in direct contact with the cavity 706 and the dielectric material 707. The protuberant antennas 708 form a pivot line 711 that is perpendicular to the plane containing FIG. 12. The dielectrophoretic force manifests itself as an easily detected torque motion of the antenna 708 about the pivot line 711.

It is to be understood that the present invention is not limited to the embodiments described above, but encompasses any and all embodiments within the scope of the following claims.

What is claimed is:

1. A detector for detecting a target inanimate entity comprising:

a detector housing having a reference material chamber housing a reference material, the reference material being selected based on the target inanimate entity; and an antenna coupled with the detector housing, wherein the antenna in accordance with the reference material reacts to a dielectrophoresis force driven by electric field patterns and spatial gradients of the target inanimate entity.

2. A detector according to claim 1, wherein said detector housing is formed of a first dielectric material.

3. A detector according to claim 2, wherein said first dielectric material is polyvinylchloride (PVC).

4. A detector according to claim 2, wherein said first dielectric material is polyurethane (PUT).

5. A detector according to claim 2, wherein said reference material is a second dielectric material.

6. A detector according to claim 2, wherein said second dielectric material is air.

7. A detector for detecting a target inanimate entity comprising:

a detector housing having a reference material chamber; and means for detecting a maximum electric field spatial gradient by a dielectrophoresis force of an electric field pattern exhibited by the target inanimate entity.

8. A method of detecting a target inanimate entity comprising detecting a maximum spatial gradient of an electric field pattern exhibited by the target inanimate entity in accordance with dielectrophoresis.

9. A method of detecting a target inanimate entity with a detector including a handle forming part of an antenna assembly; the method comprising:

holding the handle such that the detector can pivot about a pivot line defined by the handle; and acquiring a local electric field pattern spatial gradient maximum with the antenna assembly that causes the detector to pivot about the pivot line in accordance with a dielectrophoresis force.

10. A method as claimed in claim 9, further comprising increasing an operator decay time constant through electronic circuitry connected to the detector.

11. A method as claimed in claim 9, wherein the acquiring step comprises scanning the detector in a substantially linear motion back and forth.

12. A method as claimed in claim 9, wherein the detector includes a housing having a reference material chamber housing a reference material, the method comprising selecting the reference material based on the target inanimate entity.

13. A method for locating a target inanimate entity with a locating device, the method comprising detecting a polarization charge pattern in accordance with a spatially non-uniform electric field pattern by a dielectrophoresis force exhibited by the target inanimate entity.

14. A method as claimed in claim 13, further comprising increasing a decay time constant of the polarization charge pattern.

15. A method as claimed in claim 14, wherein said increasing step comprises modifying and optimizing the decay time constant.

16. A method as claimed in claim 13, further comprising attaching an antenna to a polarization unit, and tuning the locating device by pointing the antenna toward a reference entity and adjusting an axial ratio of the locating device by changing at least one of a length of the antenna and an exact relative position of the antenna compared to a position of other device components to obtain an optimum result based on a positional range from the locating device to the polarization unit.

* * * * *